United States Patent [19]
Fitz

[11] Patent Number: 6,117,104
[45] Date of Patent: Sep. 12, 2000

[54] STENT DEPLOYMENT SYSTEM AND METHOD OF USE

[75] Inventor: Matthew J. Fitz, Sunnyvale, Calif.

[73] Assignee: Advanced Cardiovascular Systems, Inc., Santa Clara, Calif.

[21] Appl. No.: 09/149,325

[22] Filed: Sep. 8, 1998

[51] Int. Cl.[7] .................................................. A61M 29/00
[52] U.S. Cl. ....................... 604/96.01; 604/509; 606/194
[58] Field of Search .............................. 604/96–104, 500, 604/508, 509; 606/192, 194, 195, 198

[56] References Cited

U.S. PATENT DOCUMENTS

| | | |
|---|---|---|
| 3,105,492 | 10/1963 | Jeckel . |
| 3,657,744 | 4/1972 | Ersek . |
| 3,993,078 | 11/1976 | Bergentz et al. . |
| 4,130,904 | 12/1978 | Whalen . |
| 4,140,126 | 2/1979 | Choudhury . |
| 4,159,719 | 7/1979 | Haerr . |
| 4,387,952 | 6/1983 | Slusher . |

(List continued on next page.)

FOREIGN PATENT DOCUMENTS

| | | |
|---|---|---|
| 0 221 570 A2 | 5/1987 | European Pat. Off. . |
| 0 380 668 | 10/1988 | European Pat. Off. . |
| 0 335 341 A1 | 10/1989 | European Pat. Off. . |
| 0 338 816 | 10/1989 | European Pat. Off. . |
| 0 357 003 A2 | 3/1990 | European Pat. Off. . |
| 0 361 192 | 4/1990 | European Pat. Off. . |
| 0 364 787 A1 | 4/1990 | European Pat. Off. . |
| 0 372 789 A3 | 6/1990 | European Pat. Off. . |
| 0 407 951 | 1/1991 | European Pat. Off. . |

(List continued on next page.)

OTHER PUBLICATIONS

Dotter, Charles T., Transluminally Placed Coilspring Endarterial Tube Grafts, *Investigative Radiology*, pp. 329–332, Sep./Oct. 1969.

Rösch, J., M.D., et al., Transjugular Intrahepatic Portacaval Shunt: An Experimental Work, *The American Journal of Surgery*, pp. 588–592, vol. 121, May 1971.

Dotter, Charles T., Transluminal Expandable Nitinol Coil Stent Grafting: Preliminary Report, *Radiology Journal*, pp. 259–260, Apr. 1983.

Cragg, et al., Non–Surgical Placement of Arterial Endoprostheses: A New Technique Using Nitinol Wire, *Radiology Journal*, pp. 261–263, Apr. 1983.

Maass, et al., Radiological Follow–Up of Transluminally Inserted Vascular Endoprostheses: An Experimental Study Using Expanding Spirals, *Radiology Journal*, pp. 659–663, 1984.

70th Scientific Assembly and Annual Meeting: Scientific Program, *Radiology*, Washington, D.C., Nov. 25–30, 1984, Special Edition, vol. 153(P).

(List continued on next page.)

*Primary Examiner*—John D. Yasko
*Attorney, Agent, or Firm*—Fulwider Patton Lee & Utecht, LLP

[57] ABSTRACT

A stent deployment catheter having an expandable section is inserted into a patient's vasculature to position the expandable section within the diseased area. Various devices can then be quickly and easily inserted within the deployment catheter precisely positioned with respect to the diseased area, and withdrawn without traumatizing vessel tissue. Inflation of a balloon within the expandable section allows a lesion to be dilated or a stent mounted on the expandable section to be expanded and implanted in the vessel.

20 Claims, 3 Drawing Sheets

U.S. PATENT DOCUMENTS

| | | |
|---|---|---|
| 4,503,569 | 3/1985 | Dotter . |
| 4,504,354 | 3/1985 | George et al. . |
| 4,512,338 | 4/1985 | Balko et al. . |
| 4,531,933 | 7/1985 | Norton et al. . |
| 4,553,545 | 11/1985 | Maass et al. . |
| 4,580,568 | 4/1986 | Gianturco . |
| 4,619,246 | 10/1986 | Molgaard-Nielsen et al. . |
| 4,649,922 | 3/1987 | Wiktor . |
| 4,650,466 | 3/1987 | Luther . |
| 4,655,771 | 4/1987 | Wallsten . |
| 4,681,110 | 7/1987 | Wiktor . |
| 4,706,671 | 11/1987 | Weinrib . |
| 4,733,665 | 3/1988 | Palmaz . |
| 4,739,762 | 4/1988 | Palmaz . |
| 4,740,207 | 4/1988 | Kreamer . |
| 4,762,128 | 8/1988 | Rosenbluth . |
| 4,767,418 | 8/1988 | Deininger . |
| 4,776,337 | 10/1988 | Palmaz . |
| 4,795,458 | 1/1989 | Regan . |
| 4,800,882 | 1/1989 | Gianturco . |
| 4,830,003 | 5/1989 | Wolff et al. . |
| 4,848,343 | 7/1989 | Wallsten et al. . |
| 4,856,516 | 8/1989 | Hillstead . |
| 4,870,966 | 10/1989 | Dellon et al. . |
| 4,877,030 | 10/1989 | Beck et al. . |
| 4,878,906 | 11/1989 | Lindemann et al. . |
| 4,886,062 | 12/1989 | Wiktor . |
| 4,892,539 | 1/1990 | Koch . |
| 4,893,623 | 1/1990 | Rosenbluth . |
| 4,907,336 | 3/1990 | Gianturco . |
| 4,913,141 | 4/1990 | Hillstead . |
| 4,922,905 | 5/1990 | Strecker . |
| 4,943,346 | 7/1990 | Mattelin . |
| 4,950,227 | 8/1990 | Savin et al. . |
| 4,963,022 | 10/1990 | Sommargren . |
| 4,969,458 | 11/1990 | Wiktor . |
| 4,969,890 | 11/1990 | Sugita et al. . |
| 4,986,831 | 1/1991 | King et al. . |
| 4,990,155 | 2/1991 | Wilkoff . |
| 4,994,071 | 2/1991 | MacGregor . |
| 4,998,539 | 3/1991 | Delsanti . |
| 5,002,560 | 3/1991 | Machold et al. . |
| 5,007,926 | 4/1991 | Derbyshire . |
| 5,015,253 | 5/1991 | MacGregor . |
| 5,019,085 | 5/1991 | Hillstead . |
| 5,019,090 | 5/1991 | Pinchuk . |
| 5,026,377 | 6/1991 | Burton et al. . |
| 5,034,001 | 7/1991 | Garrison et al. . |
| 5,035,706 | 7/1991 | Gianturco et al. . |
| 5,037,377 | 8/1991 | Alonso . |
| 5,037,392 | 8/1991 | Hillstead . |
| 5,037,427 | 8/1991 | Harada et al. . |
| 5,041,126 | 8/1991 | Gianturco . |
| 5,059,211 | 10/1991 | Stack et al. . |
| 5,061,275 | 10/1991 | Wallsten et al. . |
| 5,062,829 | 11/1991 | Pryor et al. . |
| 5,064,435 | 11/1991 | Porter . |
| 5,071,407 | 12/1991 | Termin et al. . |
| 5,073,694 | 12/1991 | Tessier et al. . |
| 5,078,720 | 1/1992 | Burton et al. . |
| 5,078,726 | 1/1992 | Kreamer . |
| 5,078,736 | 1/1992 | Behl . |
| 5,084,065 | 1/1992 | Weldon et al. . |
| 5,089,005 | 2/1992 | Harada . |
| 5,089,006 | 2/1992 | Stiles . |
| 5,092,877 | 3/1992 | Pinchuk . |
| 5,100,429 | 3/1992 | Sinofsky et al. . |
| 5,102,417 | 4/1992 | Palmaz . |
| 5,104,404 | 4/1992 | Wolff . |
| 5,108,416 | 4/1992 | Ryan et al. . |
| 5,108,417 | 4/1992 | Sawyer . |
| 5,116,318 | 5/1992 | Hillstead . |
| 5,116,360 | 5/1992 | Pinchuk et al. . |
| 5,116,365 | 5/1992 | Hillstead . |
| 5,122,154 | 6/1992 | Rhodes . |
| 5,123,917 | 6/1992 | Lee . |
| 5,133,732 | 7/1992 | Wiktor . |
| 5,135,536 | 8/1992 | Hillstead . |
| 5,158,548 | 10/1992 | Lau et al. . |
| 5,161,547 | 11/1992 | Tower . |
| 5,163,958 | 11/1992 | Pinchuk . |
| 5,171,262 | 12/1992 | MacGregor . |
| 5,180,368 | 1/1993 | Garrison . |
| 5,183,085 | 2/1993 | Timmermans . |
| 5,192,297 | 3/1993 | Hull . |
| 5,192,307 | 3/1993 | Wall . |
| 5,195,984 | 3/1993 | Schatz . |
| 5,197,978 | 3/1993 | Hess . |
| 5,222,971 | 6/1993 | Willard et al. . |
| 5,226,913 | 7/1993 | Pinchuk . |
| 5,234,456 | 8/1993 | Silverstrini . |
| 5,242,452 | 9/1993 | Inoue . |
| 5,282,823 | 2/1994 | Schwartz et al. . |
| 5,282,824 | 2/1994 | Gianturco . |
| 5,290,305 | 3/1994 | Inoue . |
| 5,292,331 | 3/1994 | Boneau . |
| 5,304,200 | 4/1994 | Spaulding . |
| 5,314,444 | 5/1994 | Gianturco . |
| 5,314,472 | 5/1994 | Fontaine . |
| 5,330,500 | 7/1994 | Song . |
| 5,356,433 | 10/1994 | Rowland et al. . |
| 5,423,885 | 6/1995 | Williams . |
| 5,851,210 | 12/1998 | Torossian . |
| 5,857,998 | 1/1999 | Barry . |

FOREIGN PATENT DOCUMENTS

| | | |
|---|---|---|
| 0 421 729 A2 | 4/1991 | European Pat. Off. . |
| 0 423 916 A1 | 4/1991 | European Pat. Off. . |
| 0 428 479 A1 | 5/1991 | European Pat. Off. . |
| 0 062 300 | 10/1992 | European Pat. Off. . |
| 0 540 290 B1 | 10/1992 | European Pat. Off. . |
| 0 517 075 | 12/1992 | European Pat. Off. . |
| 0 541 443 A1 | 5/1993 | European Pat. Off. . |
| 2 677 872 | 12/1992 | France . |
| 58-501458 | 9/1983 | Japan . |
| 62-231657 | 10/1987 | Japan . |
| 62-235496 | 10/1987 | Japan . |
| 63-214264 | 9/1988 | Japan . |
| 64-83685 | 3/1989 | Japan . |
| 1-299550 | 12/1989 | Japan . |
| 2-174859 | 7/1990 | Japan . |
| 2-255157 | 10/1990 | Japan . |
| 3-9745 | 1/1991 | Japan . |
| 3-9746 | 1/1991 | Japan . |
| 3-151983 | 6/1991 | Japan . |
| 4-25755 | 2/1992 | Japan . |
| 2 070 490 | 9/1981 | United Kingdom . |
| 2 135 585 | 9/1984 | United Kingdom . |
| WO 91/07139 | 5/1991 | WIPO . |
| WO 92/06734 | 4/1992 | WIPO . |
| WO 92/09246 | 6/1992 | WIPO . |

OTHER PUBLICATIONS

C.R. Bard, *PE Plus Peripheral Balloon Dilatation Catheter*, C.R. Bard, Inc., Aug. 1985.

Wright, et al., Percutaneous Endovascular Stents: an Experimental Evaluation, *Radiology Journal*, pp. 69–72, 1985.

Duprat, et al., Flexible Balloon–Expanded Stent for Small Vessels, *Radiology Journal*, pp. 276–278, 1987.

Charnsangavej, E., M.D., et al., Endovascular Stent for Use in Aortic Dissection: An In Vitro Experiment, *Radiology*, pp. 323–324, vol. 157, No. 2, Nov. 1985.

Palmaz, et al., Expandable Intraluminal Graft: A Preliminary Study, *Radiology Journal*, pp. 73–77, 1985.

72$^{nd}$ Scientific Assembly and Annual Meeting: RSNA Scientific Program, *Radiology*, Chicago: Nov. 30–Dec. 5, 1986, Special Edition, vol. 161(P).

Program: Day 2 (Nov. 18) The Radiological Society of North America, *Radiology*, Chicago: Nov. 30–Dec. 5, 1986, Special Edition, vol. 161(P).

Wallace, Michael J., et al., Tracheobronchial Tree: Expandable Metallic Stents Used in Experimental and Clinical Applications (Work in Progress), *Radiology*, pp. 309–312, vol. 158, Feb. 1986.

Rösch, Josef, M.D., et al., Gianturco Expandable Wire Stents in the Treatment of Superior Vena Cava Syndrome Recurring After Maximum–Tolerance Radiation, *Cancer*, pp. 1243–1246, vol. 60, Sep. 1987.

Yoshioka, Tetsuya, et al., Self–Expanding Endovascular Graft: An Experimental Study in Dogs, *American Journal of Roentgeriology*, pp. 6730676, vol. 151, Oct. 1988.

Rösch, Josef, M.D., et al., Modified Gianturco Expandable Wire Stents in Experimental and Clinical Use, *Annales de Radiologie*, pp. 100–103, vol. 31, No. 2, 1988.

Mirich, David, et al., Percutaneously Placed Endovascular Grafts for Aortic Aneurysms: Feasibility Study, *Radiology*, pp. 1033–1037, 1989 Part 2.

Yoshioka, Tetsuya, et al., Development and Clinical application of Biliary Andoprosthesis Using Expandable Metallic Stents, *Japan Radiological Society* pp. 1183–1185, vol. 48, No. 9 (with translation).

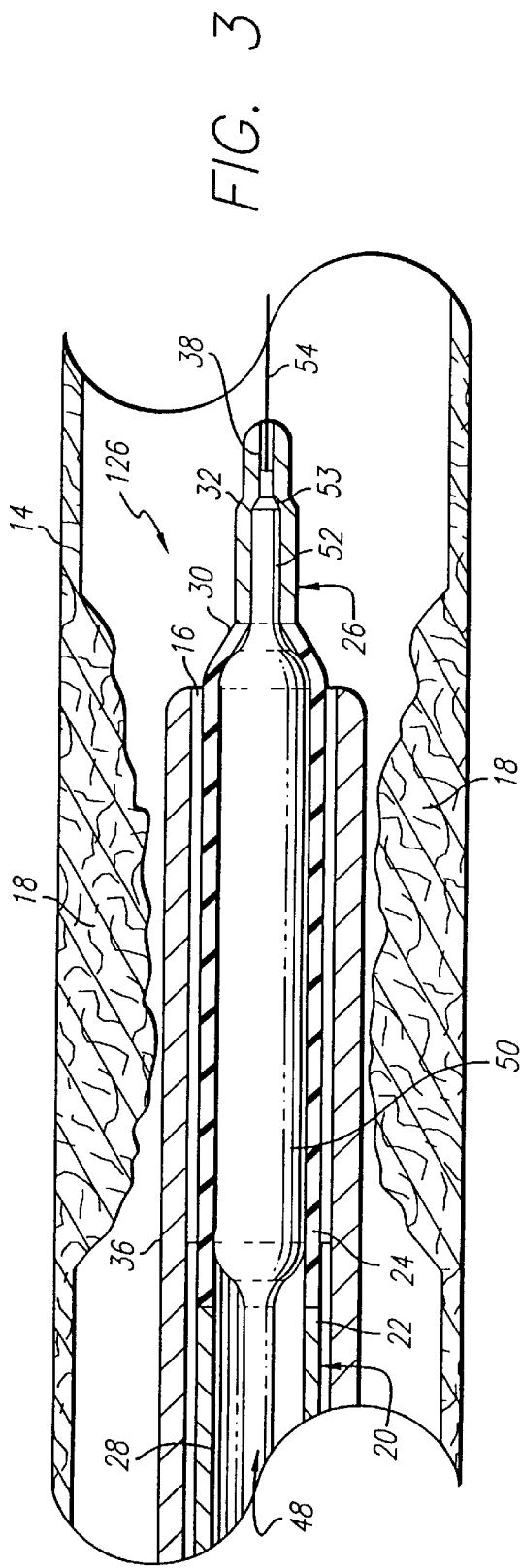
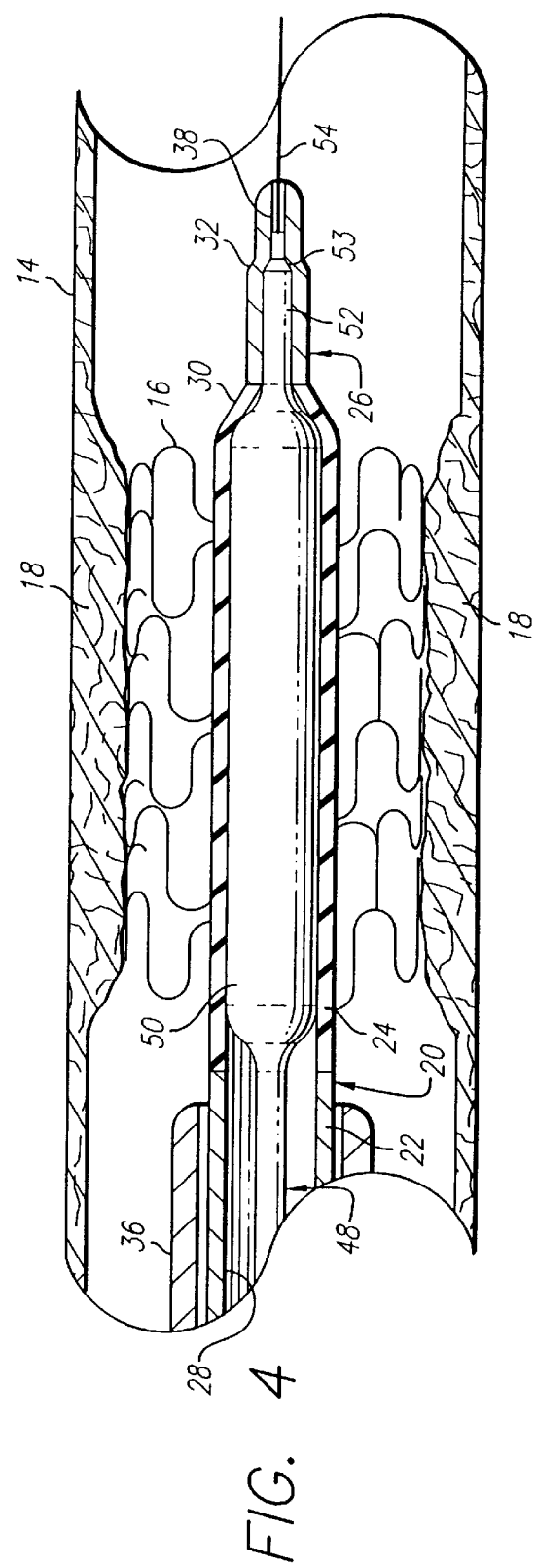

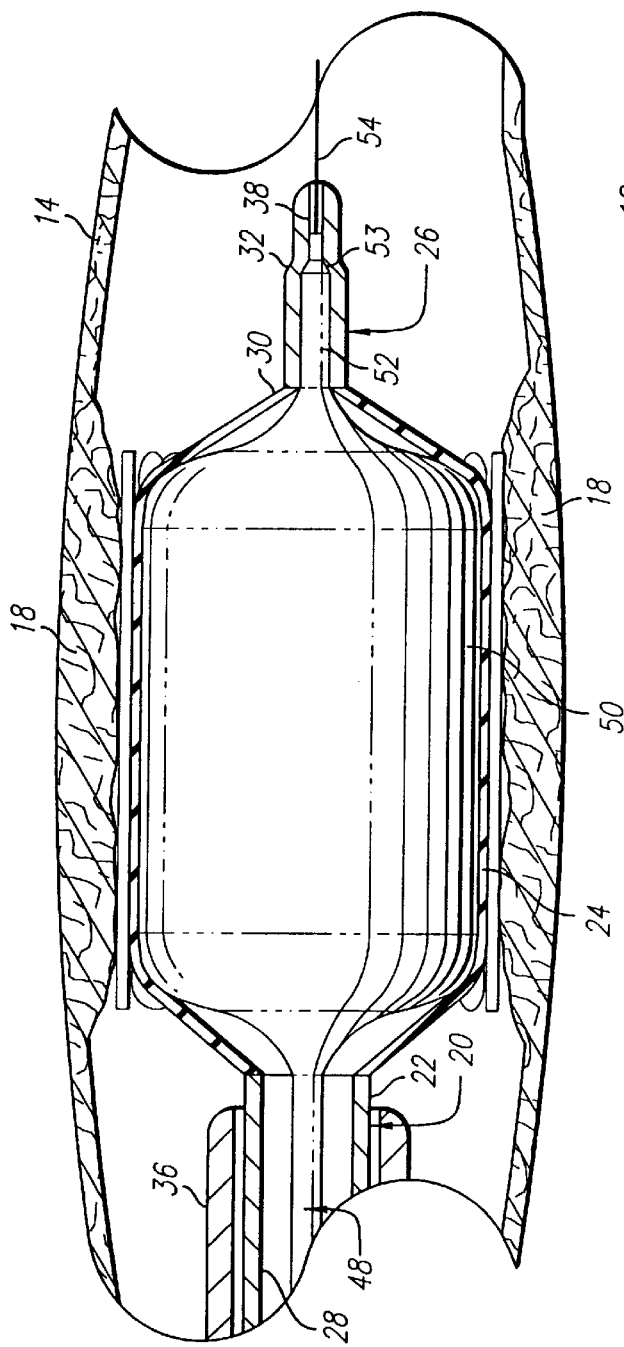
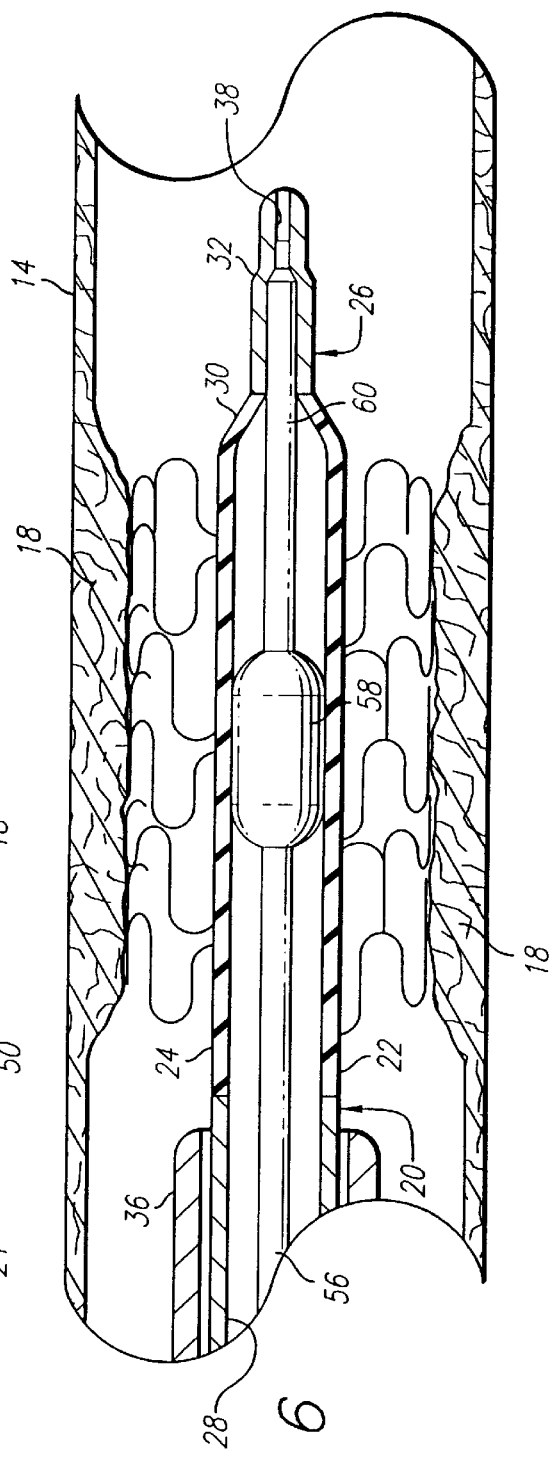

STENT DEPLOYMENT SYSTEM AND METHOD OF USE

BACKGROUND OF THE INVENTION

The present invention generally relates to stent deployment systems and more particularly pertains to deployment systems that facilitate the exchange and precise positioning of various implements at the deployment site with minimal effort and without the risk of injury to the vasculature.

Vascular therapy is often a multi-step process involving treatment with a variety of devices. Initially, angiography is performed in order to map the lesion and arterial geometry. A guiding catheter is subsequently placed into the ostium of the artery after which a small diameter guide wire is extended through the diseased legion. A low profile balloon is then advanced along the guide wire into position within the target site and inflated to pre-dilate the site. After the inner diameter of the lesioned area has been sufficiently increased, a stent deployment system is maneuvered into place. Such system may consist of a catheter carrying a self-expanding stent that is maintained in its collapsed configuration by a restraining sheath. Upon retraction of the sheath, the stent automatically expands and the deployment system in withdrawn. Subsequent thereto, a large high pressure balloon catheter is advanced through the vasculature and positioned within the expanded stent. Inflation of the balloon serves to post-dilate the stented area. Withdrawal of the balloon catheter and introduction of an ultrasound imaging catheter (IVUS) allows the success of the procedure to be assessed. The post dilation and imaging steps may have to be repeated until a satisfactory result is obtained.

A number of disadvantages are inherent in the above-described procedure. The repeated introduction, precise positioning, and withdrawal of the various devices is not only time consuming but, each time a device is shifted within the artery, the risk of dislodging embolic plaque and causing a stroke thereby is enhanced. Additionally, the failure to precisely position each newly introduced device may cause problems. For instance, an imprecisely placed high pressure balloon may not only cause the stent to become distorted, but expansion against unstented, unprotected tissue could cause injury. A poorly placed imaging catheter would not only yield poor imagery but would require further repositioning.

A stent deployment system is needed that simplifies the stent deployment procedure, expedites the operation and reduces the risk of injury to the artery as well as the risk of dislodging embolic plaque.

SUMMARY OF THE INVENTION

The present invention provides a stent deployment system that overcomes many of the shortcomings of heretofore known systems. More particularly, once the deployment system is in place, the stent can be expanded, repeatedly post-dilated and repeatedly imaged without risk of injury to the artery or risk of dislodging embolic plaque. Moreover, the system allows each successively employed device to be quickly introduced and automatically advanced to precisely the desired position.

The system of the present invention includes a non-expandable deployment catheter having an expandable section incorporated therein near its distal end. A non-expandable shaped distal tip is attached to the distal end of the expandable section. The expandable section is dimensioned to substantially conform in length to an expandable or self-expanding stent positioned thereover. Once the catheter carrying the stent thereon is properly positioned within the diseased artery, any of a variety of balloon catheters, imaging catheters or other implements can be successively inserted into the deployment catheter without the need to shift the position of the deployment catheter. Additionally, because the shape of the distal tip of the deployment catheter conforms to the shape of the distal end of the balloon catheter, imaging catheter or any other device that is to be inserted thereinto, the tip serves as a stop which positively limits the advancement of the inserted device when the balloon, imaging head or other device is precisely aligned with the position of the stent.

The expandable section allows the minimally encumbered inflation of a balloon positioned therein as well as the unhindered expansion of the stent positioned thereover. Unstented tissue is simultaneously protected due to the unexpandability of the adjacent section of catheter as well as the adjacent distal tip. The presence of the expandable material between the stent and the balloon also protects the balloon from being damaged through direct contact with the stent and serves to contain any debris should the balloon rupture. Additionally, the presence of the expandable section about the balloon limits the growth of the balloon at high pressures to reduce the risk of lesion dissection. Finally, the expandable section assists in the refolding of the balloon after deflation due to the restoring force exerted thereby to thus render the balloon catheter easier to withdraw. An optional gel coating applied to the interior surface of the catheter serves to center any catheter advanced therethrough while allowing for dimensional variations.

These and other features and advantages of the present invention will become apparent from the following detailed description of a preferred embodiments which, taken in conjunction with the accompanying drawings, illustrate by way of example the principles of the invention.

BRIEF DESCRIPTION OF THE DRAWINGS

FIG. 3 is a cross-sectional view of another embodiment of the deployment system of the present invention in position within a diseased artery prior to expansion of the stent;

FIG. 4 is a cross-sectional view of the system shown in FIG. 3 after expansion of the stent;

FIG. 5 is a cross-sectional view of the system during post-inflation; and

FIG. 6 is a cross-sectional view of the system during imaging.

DETAILED DESCRIPTION OF THE PREFERRED EMBODIMENTS

The present invention provides a stent deployment system that facilitates the placement, expansion, subsequent manipulation and imaging of a stent deployed within a vessel. The method of its use simplifies and expedites the deployment procedures and minimizes the risk of injury to the artery as well as the risk of dislodging embolic plaque. The figures illustrate various embodiments and components of the system in position within a diseased artery before and after expansion of the stent.

Figure 1:
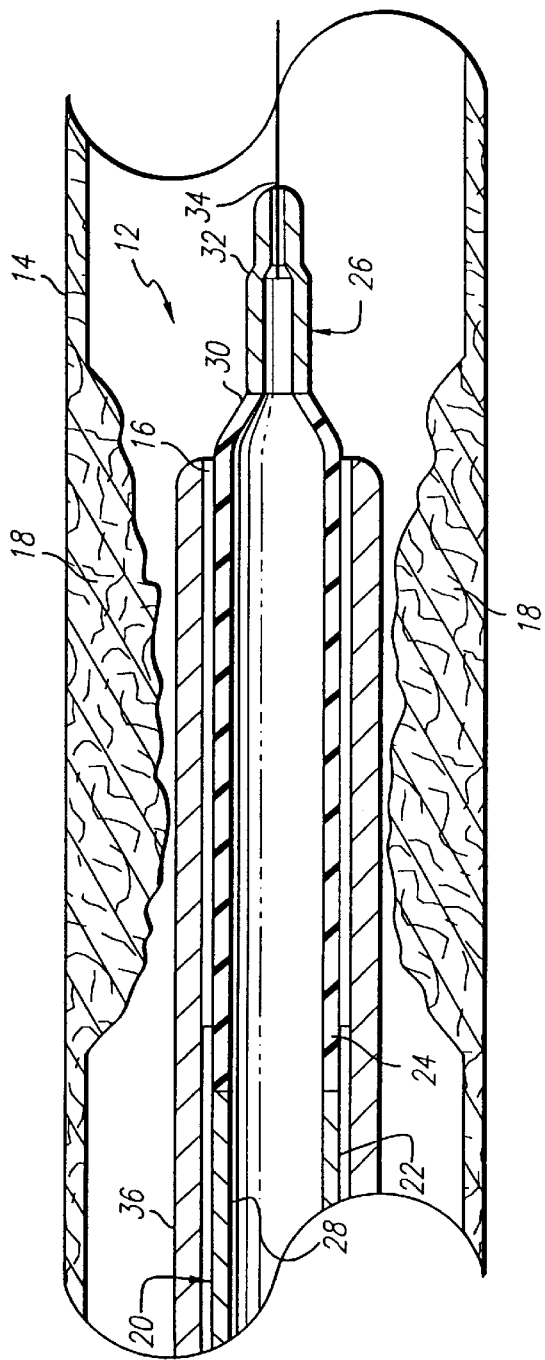
FIG. 1 is a cross-sectional view of one embodiment of the deployment system of the present invention in position within a diseased artery.

FIG. 1 is a cross-sectional view of the deployment system 12 of the present invention in position within diseased artery 14. The system has been advanced through the patient's vasculature such that stent 16 carried thereby is roughly centered within the stenosis, in this case caused by the presence of stenotic plaque 18. The deployment system includes stent deployment catheter 20 that has substantially non-expandable section 22, expandable section 24 and a substantially non-expandable shaped distal tip 26 all which define interior lumen 28. The expandable section 24, consists of an elastomeric membrane and is of a length that corresponds to the length of stent 16 positioned thereover. The non-expandable section 22 extends from the expandable section to the proximal end of the catheter while tip 26 defines the distal end of the catheter. The tip preferably has one or two necked down sections that define one or two reductions in diameter 30, 32 and terminates in a length of guide wire 34 extending distally therefrom. To maintain stent 16 in position over elastomeric membrane segment 24 and to maintain the stent in its collapsed configuration, retractable sheath 36 is fitted along the catheter and over the stent.

Figure 2:
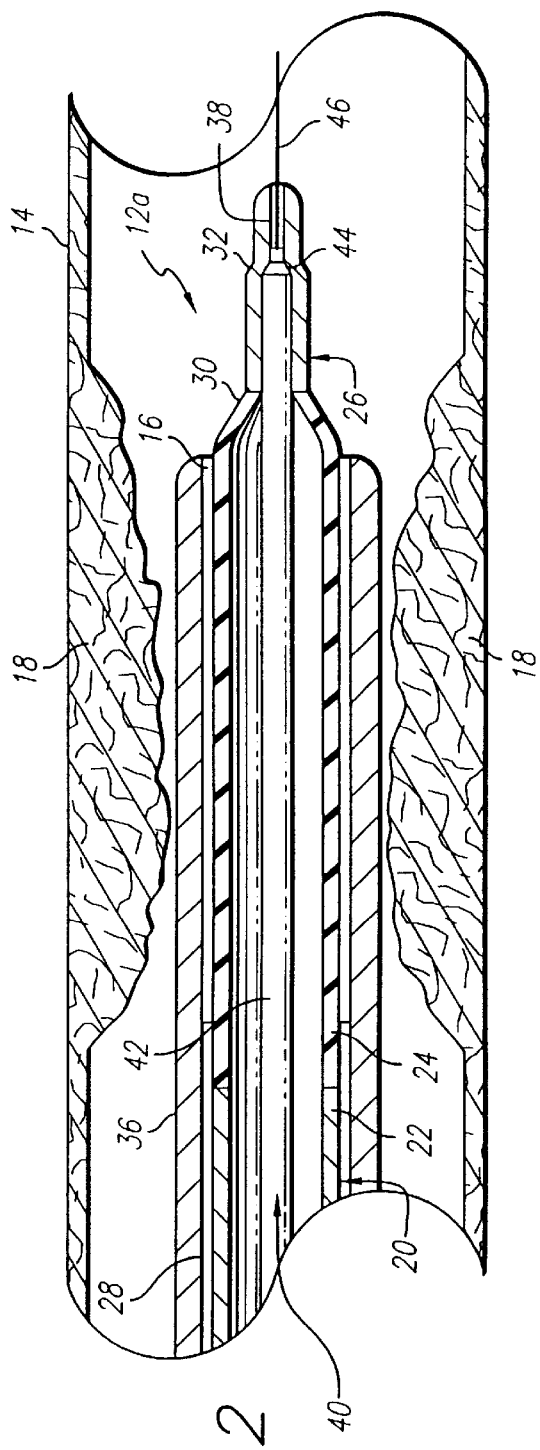
FIG. 2 is a cross-sectional view of another embodiment of the deployment system of the present invention in position within a diseased artery.

FIG. 2 illustrates an alternative embodiment configuration 12a of the deployment system wherein an orifice 38 that extends lumen 28 through the distal end of distal tip 26 replaces rigidly affixed guide wire 34 of the embodiment shown in FIG. 1. A removable guidance device 40 is shown in position within lumen 28. The guidance device includes shaft 42 that extends proximally and protrudes from catheter 22 at a position outside the vasculature so as to enable it to be manipulated. The shaft is constructed to be trackable yet pushable and has a distal end profile 44 that conforms to the profile of one or both reductions in diameter of distal tip 26. The interaction of the distal end of the shaft with the interior of the distal tip serves to positively limit the distal movement of the guidance device within lumen 28. Extending from the distal end of the shaft and through orifice 38 is a length of guide wire of a conventional diameter (e.g., 0.014", 0.018", or 0.035"), specifically selected for a particular application.

FIG. 3 illustrates another alternative embodiment configuration 12b of the deployment system wherein guidance device 40 shown in FIG. 2 is replaced by balloon catheter 48. Such catheter includes inflatable balloon 50 located near its distal end, distal section 52 extending distally from the balloon and optionally, guide wire 54 extending distally from the distal section. The balloon is dimensioned to conform in length to expandable section 24. Its diameter in its uninflated state is such to allow it to be advanced and withdrawn through lumen 28. A lumen extending within the balloon catheter places the interior of the balloon into fluid communication with the proximal end of the catheter to facilitate inflation and deflation of the balloon. The diameter of distal section 52 is selected to be greater than that of orifice 38 and its end profile may conform to one or both of necked down surfaces 30,32 formed within the distal tip. The length of the distal section is selected such that balloon 50 becomes precisely positioned within expandable section 24 upon engagement of distally facing surface or surfaces 53 of distal section 52 with one or more interior surfaces of distal tip 26. The guide wire 54, affixed to distal section 52 is of a length and diameter specifically selected for a particular application.

Optionally, lumen 28 may be coated with a gel in order to provide a lubricated surface for more easily inserting and withdrawing implements. If a sufficiently thick layer is built up, such gel coating would also serve to center the inserted implement within the lumen while allowing for dimensional variations.

The deployment system of the present invention is employed after a number of preliminary steps have been completed. Angiography is first performed to map the lesion and arterial geometry. The appropriately sized guide wire is then selected and advanced through the vasculature and through the diseased lesion. A low-profile balloon is subsequently advanced to the site and inflated to pre-dilate the stenosed area.

At this point, the deployment system of the present invention is advanced through the vasculature either over the previously placed guide wire or by a combination of components that include a guide wire such as illustrated in FIGS. 1, 2 or 3. Use of an embodiment wherein the guide wire is not fixed to the distal end of the deployment system readily allows any guide wire carrying components (e.g. a guidance device 40 or a balloon catheter 48) to be exchanged for ones with a different size guide wire should an attempt to use the originally selected component prove to have too small or too large a wire diameter. The use of the deployment system of the present invention allows such exchange to be achieved without withdrawing the catheter thereby avoiding the risk of inflicting any injury on the vessel walls. Insertion of the newly selected insert is also accomplished without any trauma and the implement is very quickly advanceable to the tip of the deployment catheter.

Once it is established that deployment catheter 20 is in position, such as by fluoroscopic means, self-expanding stent 16 is deployed by retraction of sheath 36 as is shown in FIG. 4. The stent expands to disengage from the catheter 20 and engage the stenosis. Depending upon the type of stenosis involved, stenotic plaque 18 may thereby become somewhat compressed as is shown in FIG. 4 or artery 14 may become somewhat distended or both. Automatic expansion of the stent may be accomplished with or without an implement present within lumen 28. However, most preferably, dilation balloon catheter 48 is already in place so that post dilation can be accomplished immediately upon expansion of the stent. It is therefore preferred that the system is configured as is shown in FIG. 3 just prior to expansion of the stent. Alternatively, a guide wire-less balloon catheter inserted within guide wire 34 tipped deployment catheter 20 shown in FIG. 1 may be used.

Once the stent has been allowed to self expand, it is subjected to post-dilation by the inflation of high pressure balloon 50 located within deployment catheter 20, and more particularly, positioned within expandable section 24. This step is illustrated in FIG. 5 wherein the balloon is shown distending expandable section 24 of catheter 20 as well as the surrounding stent 16. The figure additionally shows the further compression of stenotic plaque 18 as well as a slight distention of artery 14. Ideally, the interior diameter of deployed stent 16 will substantially correspond to the interior diameter of the healthy artery 14.

After post dilation has been achieved, balloon 50 is deflated prior to its removal. The restoring force generated by the distended elastomeric membrane of expandable section 24, serves to expedite deflation and fold the balloon into a fairly compact configuration typically along the same fold lines with which it was originally delivered. Once the balloon is deflated and compacted by the action of the elastomeric membrane, balloon catheter 48 is easily withdrawn from deployment catheter 20. This of course is achieved without any frictional contact with the surrounding tissue as the deployment catheter 20 remains stationary.

An imaging catheter 56 is subsequently inserted into deployment catheter 20 as is shown in FIG. 6, whereby its distal section 60 serves to precisely position imaging head 58 within expandable section 24. Examination of the stented region will allow a determination to be made if additional treatment is required or if the procedure is complete and the catheter can be withdrawn. If additional dilation is required, imaging catheter 56 is withdrawn and a balloon catheter is reinserted with a balloon that is either of a different size, pressure capability or compliance. After inflation and deflation, the area is again imaged to determine whether the process has to be repeated. If satisfactory results have been achieved the entire deployment system is withdrawn from the patient to complete the procedure.

The non-expandable section 22 and catheter tip 26 are constructed in a manner and using materials as are well known in the art. The elastomeric membrane may be formed of soft plastics such as silicone, DFLEX®, TICOFLEX®, rubber, nylon, polyethylene, polyolifin, PEBAX®, or HYTREL®. The sheath 36, stent and insertable implements are constructed by conventional means as are well known in the art.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. A stent deployment system for transporting a stent to a deployment site and expanding the stent at the site, comprising:
   a substantially non-expandable deployment catheter having an expandable section incorporated therein near a distal end thereof, said expandable section being dimensioned to substantially conform in length to a stent positioned thereabout;
   a balloon catheter having an inflatable balloon and being removably positioned within said expandable section of said deployment catheter; said expandable section being sufficiently expandable to enable said inflatable balloon to be inflated therein to expand said stent.

2. The deployment system of claim 1, wherein said expandable section comprises an elastic membrane.

3. The deployment system of claim 1, wherein said deployment catheter defines a lumen that is closed at its distal end.

4. The deployment system of claim 3, wherein a guide wire is affixed to and extends distally from the distal end of said deployment catheter.

5. The deployment system of claim 4, further comprising a retractable sheath that extends over a stent positioned about said expandable section so as to maintain such stent in position and in a collapsed configuration, whereby retraction of said sheath allows such stent to expand or to be expanded.

6. The deployment system of claim 4, further comprising a balloon catheter including an inflatable balloon dimensioned to be insertable into said deployment catheter and advanceable therethrough to a position such that said balloon is aligned with said expandable section.

7. The deployment system of claim 6, wherein said balloon catheter is configured to engage said closed end of said lumen when said balloon is aligned with said expandable section.

8. The deployment system of claim 4, further comprising an imaging catheter including an imaging head dimensioned to be insertable into said deployment catheter and advanceable therethrough to a position that enables imaging of the deployment site.

9. The deployment system of claim 8, wherein said imaging catheter is configured to engage said closed end of said lumen when said imaging head is properly positioned.

10. The deployment system of claim 1, wherein said deployment catheter defines a lumen of a first diameter and said catheter has a distal tip that necks down to an orifice having a second diameter that is smaller than said first diameter.

11. The deployment system of claim 10, further comprising a retractable sheath extending over said stent positioned about said expandable section so as to maintain said stent in position and in a collapsed configuration, whereby retraction of said sheath allows said stent to expand or to be expanded.

12. The deployment system of claim 10, further comprising a balloon catheter including an inflatable balloon dimensioned to be insertable into said deployment catheter and advanceable therethrough to a position such that said balloon is aligned with said expandable section.

13. The deployment system of claim 12, wherein said balloon catheter is configured to engage said necked down distal tip when said balloon is aligned with said expandable section.

14. The deployment system of claim 13, wherein a guide wire is affixed to the distal end of said balloon catheter to extend through said orifice and project distally therefrom when said balloon catheter engages said necked down distal tip.

15. The deployment system of claim 10, further comprising an imaging catheter including an imaging head dimensioned to be insertable into said deployment catheter and advanceable therethrough to a position that enables imaging of the deployment site.

16. The deployment system of claim 15, wherein said imaging catheter is configured to engage said closed end of said lumen when said imaging head is properly positioned.

17. The deployment system of claim 10, further comprising a guidance device dimensioned to be insertable into said deployment catheter and advanceable therethrough to position abutting said necked down distal tip and wherein said guidance device has a guide wire distally extending therefrom and through said orifice.

18. A method of deploying a stent within an artery, comprising:
   providing a substantially non-expandable stent deployment catheter having an expandable section near a distal end thereof and defining a lumen therein, and having an expandable stent fitted about said expandable section;
   advancing said deployment catheter through the artery so that said stent is positioned within a target area;
   providing a balloon catheter having an inflatable balloon and being removably positioned within the expandable section;
   aligning said inflatable balloon within said expandable section;
   inflating the inflatable balloon of the balloon catheter to expand said expandable section and said stent;
   deflating said inflatable balloon; and
   withdrawing said balloon catheter from the artery.

19. The method of claim 18, further comprising:
   withdrawing said balloon catheter from said deployment catheter after deflation of the balloon;
   inserting an imaging catheter having an imaging head incorporated therein into said lumen thereby positioning said imaging head within said expandable section; and
   creating an image of said expanded stent within the target site.

20. The method of claim 19, further comprising:

analyzing said image to determine whether further expansion of the target site is necessary;

withdrawing said imaging catheter from said lumen upon creating said image;

inserting a second balloon catheter into said deployment catheter to position a second balloon thereon within said expandable section;

inflating said second balloon to further expand said stent;

deflating said balloon and withdrawing said second balloon catheter from said lumen of said deployment catheter;

inserting said imaging catheter and creating a second image of said expanded stent within the target site; and withdrawing said imaging catheter and said deployment catheter from the artery.

* * * * *